(12) United States Patent
Kemp et al.

(10) Patent No.: US 6,436,891 B1
(45) Date of Patent: Aug. 20, 2002

(54) ADDUCT HAVING AN ACIDIC SOLUTION OF SPARINGLY-SOLUBLE GROUP IIA COMPLEXES

(75) Inventors: Maurice Clarence Kemp, El Dorado Hills; Robert B. Lalum, Citrus Heights; Zhong Wei Xie, Folsom; Michael A. Cunha, Roseville, all of CA (US); Robert H. Carpenter, Bastrop, TX (US); Zhang Shu; Yao Yu, both of Roseville, CA (US); David E. Lewis, Eau Claire, WI (US)

(73) Assignee: Mionix Corporation, Rocklin, CA (US)

( * ) Notice: Subject to any disclaimer, the term of this patent is extended or adjusted under 35 U.S.C. 154(b) by 0 days.

(21) Appl. No.: 09/500,474

(22) Filed: Feb. 9, 2000

Related U.S. Application Data

(63) Continuation-in-part of application No. 09/253,482, filed on Feb. 19, 1999, now abandoned.

(51) Int. Cl.$^7$ ............................. C11D 7/06; C11D 7/08
(52) U.S. Cl. .................. 510/435; 510/111; 510/218; 510/252; 510/269; 510/272; 510/492
(58) Field of Search ................... 510/111, 218, 510/252, 269, 272, 435, 492

(56) References Cited

U.S. PATENT DOCUMENTS

| | | | |
|---|---|---|---|
| 5,264,017 A | | 11/1993 | Van De Walle ................ 71/61 |
| 5,571,336 A | * | 11/1996 | Wurzburger et al. ........... 134/2 |
| 5,830,838 A | * | 11/1998 | Wurzburger et al. ........ 510/254 |
| 5,895,782 A | * | 4/1999 | Overton et al. ............. 510/254 |
| 6,331,514 B1 | * | 12/2001 | Wurzburger et al. ........ 510/254 |

FOREIGN PATENT DOCUMENTS

| | | | |
|---|---|---|---|
| EP | WO 00/48469 | * | 8/2000 |
| JP | 63282117 | * | 11/1988 |
| JP | JP 63282116 | | 11/1998 |
| WO | WO 96/15666 | | 1/1996 |
| WO | WO 90 05458 | | 5/1999 |
| WO | WO 99 23896 | | 5/1999 |

OTHER PUBLICATIONS

Taiwan Patent Office, Decision of Patent Examination, issued Apr. 4, 2001.
U.S. Patent and Trademark Office, International Preliminary Examination Report, issued May 2, 2001.

* cited by examiner

*Primary Examiner*—Mark Kopec
*Assistant Examiner*—Brian P Mruk
(74) *Attorney, Agent, or Firm*—Jackson Walker L.L.P.

(57) ABSTRACT

An adduct that has an acidic solution of sparingly-soluble Group IIA complexes ("AGIIS") and at least one additive. The AGIIS can be prepared by mixing a mineral acid (such as sulfuric acid), and a Group IIA hydroxide (such as calcium hydroxide) or a Group IIA salt of a dibasic acid (such as calcium sulfate), or a mixture of the two Group IIA compounds, followed by removing the solid formed. The additives can be an alcohol, an organic acid or a surface active agent. The composition has various uses, including cleaning, food production, decontamination, bioremediation, agricultural application, medical application, and detoxification of substances.

3 Claims, 1 Drawing Sheet

ADDUCT HAVING AN ACIDIC SOLUTION OF SPARINGLY-SOLUBLE GROUP IIA COMPLEXES

This application is a continuation-in-part of an application filed Feb. 19, 1999, Ser. No. 09/253,482, the entire content of which is incorporated by reference.

BACKGROUND

This invention relates to an adduct, a composition having an acidic solution of sparingly-soluble group IIA complexes ("AGIIS") and at least one additive, to its preparation, and to its uses.

In the late 80's and early 90's, researchers in Japan developed strong ionized water ("SIW") as disinfectants. The SIW was established as water with pH 2.7 or less, having an oxidation-reduction potential of 1,000 mv or more, and chlorine concentration of 0.8 ppm or more. The SIW is prepared by electrolysis of water.

Electrolysis of tap water has also been used to produce "strong acid water" and "strong alkali water" both of which were claimed to have antiseptic properties.

U.S. Pat. No. 5,830,838 to Wurzburger, et al. describes a solution for cleaning metal surfaces. The solution is prepared by mixing calcium hydroxide and potassium hydroxide with equivalent of sulfuric acid in water then passing the solution through a 10 micron filter. The resulting concentrate can be diluted depending on the degree of surface oxidation of the metal to be treated.

U.S. Pat. No. 5,895,782 to Overton, et al. describes a solution for cleaning metal surfaces particularly non-ferrous alloys such as copper, brass and high strength aluminum alloys. The solution is prepared by mixing $Ca(OH)_2$ and KOH with equivalent sulfuric acid in water then passing the solution through a 10 micron filter. The resulting concentrate can be used full strength or diluted depending on the degree of surface oxidation of the metal to be treated.

International Publication WO 94/09798 describes a pharmaceutical composition for treatment of disease, injury and other disorders. The pharmaceutical composition comprises a complex of a calcium-containing component and a sulfate-containing component in a pharmaceutically acceptable carrier. The reference teaches the isolation from natural materials, such as peat, the inorganic compositions. The inorganic preparations comprise an alkaline, aqueous or organic, or mixture thereof, extract of peat. Peat is extracted with aqueous solutions, organic solutions or water-miscible organic solvents at temperature from below room temperature up to the boiling point of the solvents. The preferred extracting solvents are those having a pH of at least 9. Biologically active constituents of fractionated peat preparations were identified as $CaSO_4.2H_2O$ (gypsum), $CaSO_4.K_2SO_4.H_2O$ (syngenite, also referred to as the double salt of gypsum) and $K_3Na(SO_4)_2$ (apthitalite) by X-ray powder diffraction analysis. The reference also describes the synthesis of syngenite.

Chemists describe and measure the ability of a substance to donate protons [$H^+$] to a chemical reaction as the pka of that substance where

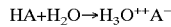

Although a hydronium ion is usually represented by $H^+$ or $H_3O^+$, but its true formula is not certain. The aggregate could be $H_5O_2^+$, $H_7O_3^+$, or even $H_9O_4^+$.

The ability to produce large quantities of positively charged water would be extremely important in a large number of applications where water is the medium of the reaction. Positively charged water has the ability to donate protons [$H^+$]. The donation of a proton is usually an intermediate step in any acid hydrolysis reaction. Acids are usually the chemical reagent used to donate protons in an aqueous solution. If the water could be the source of the [$H^+$], then there would be fewer unwanted by-products (toxins) from the reactions and there would be less hazard associated with these products use.

A strong acid is used to neutralize and remove the lime, or quicklime, from the brick and mortar. A strong acid, such as hydrochloric acid, also known as muriatic acid, is also used to clean hard water spots on shower stalls, windows, glass, toilets, urinals, mirrors and other surfaces. Hydrochloric acid is used to de-scale water towers and heat exchangers and to adjust the pH of the waste water effluent.

A full strength mineral acid, such as hydrochloric acid, is extremely corrosive to many substances, including metals. In addition, hydrochloric acid at a low pH of 0.5 or so will burn a human skin in seconds. The acid is also very harmful in that it emits fumes irritating to mucous membrane. If left near other chemicals, like bleach, hydrochloric acid will interact with them, even through a typical plastic bottle.

It is thus desirable to be able to have source of "acidity," or $H_3O^+$, without these unwanted disadvantages and be able to reduce environmental and safety hazards associated with acid hydrolysis. Preferably, this source of "acidity" should be able to prevent re-contamination following decontamination, not induce bacterial resistance, not alter the taste, color or smell of treated foodstuffs, not create any odor, effective in water in a wide range of temperatures, relatively free of danger when overdosed, can be neutralized after use, not carcinogenic or mutagenic, non-toxic, almost harmless in water and the environment, environmentally friendly, and can be stored for a long period of time without decomposition or turning into hazardous compound.

The control of microbial growth is necessary in many practical situations, and significant advances in agriculture, medicine and food science have been made through study of this area of microbiology. "Control of growth" means to prevent growth of microorganisms. This control is effected in one of two basic ways: (1) By killing microorganisms; or (2) by inhibiting the growth of microorganisms. Control of growth usually involves the use of physical or chemical agents which either kill or prevent the growth of microorganisms. Agents which kill cells are called "cidal" agents; agents which inhibit the growth of cells, but without killing them, are referred to as "static" agents. Thus the term "bactericidal" refers to killing bacteria and "bacteriostatic" refers to inhibiting the growth of bacterial cells. A "bactericide" kills bacteria, a "fungicide" kills fungi. "Sterilization" is the complete destruction or elimination of all viable organisms in or on an object being sterilized. The object is either sterile or not, there are no degrees of sterilization. Sterilization procedures involve the use of heat, radiation or chemicals, or physical removal of microorganisms.

Microorganisms tend to colonize and replicate on different surfaces resulting in adherent heterogenous microbial accumulations termed "biofilms." Biofilms may form on surfaces of food substances, feed substances, and instrumentations. The microorganisms in the biofilms may include bacteria, fungi, viruses, and protozoans. Since food safety is a national priority, any product that can help by solving a multitude of problems associated with food production is desirable. Removal and control of biofilms which harbor dangerous microbial contamination is a sanitation goal that needs to be achieved. It is also desirable to be able to safely decontaminate water and nutriment by lowering pH to levels where contaminants would react and organisms cannot live.

As used herein, the term "nutriment" means something that nourishes, heals, or promotes growth and repair the natural wastage of organic life. Thus, food for a human and feed for an animal are all examples of nutriment. Other examples of nutriment include beverages, food additive, feed additive, beverage additive, food supplement, feed supplement, beverage supplement, seasoning, spices, flavoring agent, stuffing, food dressing, pharmaceutical, biological product, and others. The nutriment can be of plant origin, animal origin, or synthetic. Current sanitizing, disinfectants and pesticides products on the market for these uses contain residues of chlorine, ammonia, organic iodine, metal salts and other deleterious residues. It is desirable to have a way that would preclude these residues by promoting acid hydrolysis without the presence of deleterious chemicals. Additionally, this method should generate few hazardous volatile gases. Importantly, it is highly desirable to have a composition that can control and the growth of, and kill, microorganisms and, at the same time, destroy the products, such as toxins, generated by, or associated with, the microorganisms.

SUMMARY

One embodiment of the present invention involves an adduct which is a composition containing a acidic solution of sparingly-soluble Group IIA complex ("AGIIS") and an additive. In a way, the additive enhances, and is synergistic to, the effectiveness of the AGIIS. Other aspects of the present invention pertain to different methods to promote the safe, clean, and environmentally sensitive ways of chemical production, pharmaceutical production, cleaning, food production, decontamination, bioremediation, agricultural application, medical application, and detoxification of a wide variety of substances.

DETAILED DESCRIPTION

Figure 1:
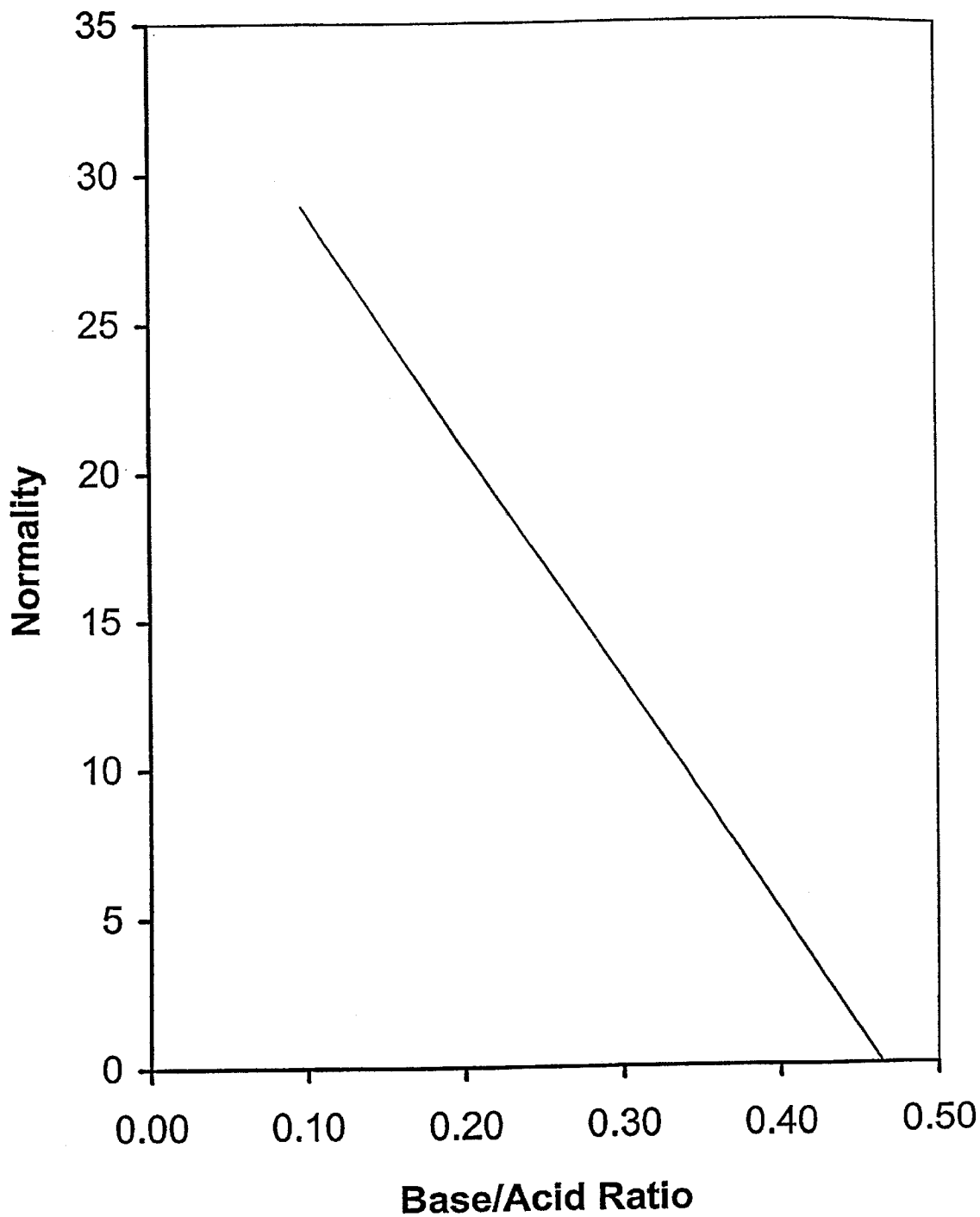
FIG. 1 shows the relation of the desired final acid normality of AGIIS and the mole ratio of calcium hydroxide to sulfuric acid, given in moles of calcium hydroxide per mole of sulfuric acid.

One aspect of the present invention pertains to an adduct containing an acidic, or low pH, solution of sparingly-soluble Group IIA complexes ("AGIIS") and an additive. The solution may have a suspension of very fine particles and the term "low pH" means the pH is below 7, in the acidic region. The AGIIS of the present invention with a certain acid normality does not have the same dehydrating behavior as a saturated calcium sulfate in sulfuric acid having the same normality. In other words, the AGIIS of the present invention with a certain acid normality does not char sucrose as readily as does a saturated solution of calcium sulfate in sulfuric acid having the same normality. Further, the AGIIS is non-volatile at room temperature. It is less corrosive to a human skin than sulfuric acid saturated with calcium sulfate having the same acid normality. Not intending to be bound by the theory, it is believed that one embodiment of AGIIS comprises near-saturated, saturated, or super-saturated calcium, sulfate anions or variations thereof, and/or complex ions containing calcium, sulfates, and/or variations thereof.

The term "complex," as used herein, denotes a composition wherein individual constituents are associated. "Associated" means constituents are bound to one another either covalently or non-covalently, the latter as a result of hydrogen bonding or other inter-molecular forces. The constituents may be present in ionic, non-ionic, hydrated or other forms.

The acidic solution of sparingly-soluble Group IIA-complex salt ("AGIIS") can be prepared in several ways. Some of the methods involve the use of Group IA hydroxide but some of syntheses are devoid of the use of any added Group IA hydroxide, although it is possible that a small amount of Group IA metal may be present as "impurities." The preferred way of manufacturing AGIIS is not to add Group IA hydroxide to the mixture. As the phrase implies, AGIIS is highly acidic, ionic, with a pH of below about 2.

Wurzburger, et al. in U.S. Pat. No. 5,830,838 describes an acidic solution prepared by the "calcium-hydroxide/potassium-hydroxide method." The solution is produced by first adding two moles of concentrated sulfuric acid (93%) to 2 liters of de-ionized water. Separately, an aqueous solution of base is prepared by adding one mole of calcium hydroxide (hydrated lime) and two moles of potassium hydroxide to 20 liters of de-ionized water with stirring. The acid solution is then mixed with the base solution. The mixture is then filtered through a 10 micron filter to remove particles of calcium sulfate or potassium sulfate of eleven microns or larger. The resulting concentrate can be used full strength or diluted with water depending on the metal surfaces to be treated. Sodium hydroxide may be used in place of potassium hydroxide. Hydrated calcium oxide may be used in place of calcium hydroxide. Another source of the base is calcium metal. In either case and as one embodiment of this application, the resultant solution is a highly acidic solution. This highly acidic solution can be diluted with water to adjust its pH to a desired higher value, i.e. less acidic.

Another way of preparing the acidic solution is by the "calcium-metal method" which involves reacting concentrated sulfuric acid with calcium metal followed by filtration. One mole of concentrated sulfuric acid was diluted with 40 moles of de-ionized water. Then, one mole of calcium metal turnings was slowly added with stirring into the solution of sulfuric acid. The stirring was continued until essentially all metal had dissolved. The resultant mixture was allowed to settle for about 5 to 6 hours before the supernatant was filtered through a 10 micron filter. The concentrate thus obtained had a pH value of about 0.5. This concentrate of hydronium ions was then diluted with de-ionized water to the desired pH value, such as pH of about 1 or about 1.8.

Then, there is the "calcium-hydride method" which involves reacting concentrated sulfuric acid and calcium hydride in water. One mole of concentrated sulfuric acid was diluted with 40 moles of de-ionized water. With agitation, 1 mole of calcium hydride was slowly added to the solution of sulfuric acid. The agitation was continued until the calcium hydride has essentially all dissolved. After the dissolution, the mixture was then allowed to settle for about 5 to 6 hours, at that time the supernatant was filtered through a 10 micron filter. The concentrate thus obtained had a pH value of about 0.1 to about 0.2, and can be further diluted.

One product from the "calcium-metal method" or "calcium-hydride method" having a pH of from −0.2 to −0.3, and from 1.4 to 1.5 acid normality gave the following analyses: Ca, 763 ppm; $SO_4$, 84633 ppm; Na, 4.76 ppm; K, 3.33 ppm; and Mg, 35.7 ppm.

The "calcium-metal method" and the "calcium-hydride method" have certain drawbacks. In each of these methods, thermal control is very difficult to achieve because of the large amount of heat generated when concentrated sulfuric acid is reacted with either calcium metal or calcium hydride. The difficulties in thermal control of the reactions cause the reactions to be difficult to reproduce and hard to control.

The preferred method of preparing AGIIS involves mixing a mineral acid with a Group IIA hydroxide, or with a Group IIA salt of a dibasic acid, or with a mixture of the two Group IIA materials. In the mixing, a salt of Group IIA is also formed. Preferably, the starting Group IIA material or materials selected will give rise to, and form, the Group IIA salt or salts that are sparingly soluble in water. The preferred mineral acid is sulfuric acid, the preferred Group IIA hydroxide is calcium hydroxide, and the prefer Group IIA salt of a dibasic acid is calcium sulfate. Other examples of Group IIA salt include calcium oxide, calcium carbonate, and "calcium bicarbonate."

Thus, for example, AGIIS can be prepared by mixing or blending starting materials given in one of the following scheme with good reproducibility:
(1) $H_2SO_4$ and $Ca(OH)_2$;
(2) $H_2SO_4$, $Ca(OH)_2$, and $CaCO_3$;
(3) $H_2SO_4$, $Ca(OH)_2$, $CaCO_3$, and $CO_2$ (gas);
(4) $H_2SO_4$ and $CaCO_3$;
(5) $H_2SO_4$, $CaCO_3$, and $Ca(OH)_2$;
(6) $H_2SO_4$, $CaCO_3$, and $CO_2$ (gas);
(7) $H_2SO_4$ and $CaSO_4$;
(8) $H_2SO_4$, $Ca(OH)_2$, and $CaSO_4$;
(9) $H_2SO_4$, $CaSO_4$, and $CaCO_3$;
(10) $H_2SO_4$, $CaSO_4$, $CaCO_3$, and $Ca(OH)_2$;
(11) $H_2SO_4$, $CaSO_4$, $CaCO_3$, and $CO_2$ (gas); and
(12) $H_2SO_4$, $CaSO_4$, $CaCO_3$, $CO_2$ (gas), and $Ca(OH)_2$.

Thus, preferably, AGIIS is prepared by mixing calcium hydroxide with concentrated sulfuric acid, with or without an optional Group IIA salt of a dibasic acid (such as calcium sulfate) added to the sulfuric acid. The optional calcium sulfate can be added to the concentrated sulfuric acid prior to the introduction of calcium hydroxide into the blending mixture. The addition of calcium sulfate to the concentrated sulfuric acid appears to reduce the amount of calcium hydroxide needed for the preparation of AGIIS. Other optional reactants include calcium carbonate and gaseous carbon dioxide being bubbled into the mixture. Regardless of the use of any optional reactants, it was found that the use of calcium hydroxide is desirable.

One preferred method of preparing AGIIS can be described briefly as: Concentrated sulfuric acid is added to chilled water (8°–12° C.) in the reaction vessel, then, with stirring, calcium sulfate is added to the acid in chilled water to give a mixture. Temperature control is paramount to this process. To this stirring mixture is then added a slurry of calcium hydroxide in water. The solid formed from the mixture is then removed. This method involves the use of sulfuric acid, calcium sulfate, and calcium hydroxide, and it has several unexpected advantages. Firstly, this reaction is not violent and is not exceedingly exothermic. Besides being easy to control and easy to reproduce, this reaction uses ingredients each of which has been reviewed by the U.S. Food and Drug Administration ("U.S. FDA") and determined to be "generally recognized as safe" ("GRAS"). As such, each of these ingredients can be added directly to food, subject, of course, to certain limitations. Under proper concentration, each of these ingredients can be used as processing aids and in food contact applications. Their use is limited only by product suitability and Good Manufacturing Practices ("GMP"). The AGIIS so prepared is thus safe for animal consumption, safe for processing aids, and safe in food contact applications. Further, the AGIIS reduces biological contaminants in not only inhibiting the growth of, and killing, microorganisms but also destroying the toxins formed and generated by the microorganisms. The AGIIS formed can also preserve, or extend the shelf-life of, consumable products, be they plant, animal, pharmaceutical, or biological products. It also preserves or improves the organoleptic quality of a beverage, a plant product or an animal product. It also possesses certain healing and therapeutic properties.

The sulfuric acid used is usually 95–98% FCC Grade (about 35–37 N). The amount of concentrated sulfuric acid can range from about 0.05 M to about 18 M (about 0.1 N to about 36 N), preferably from about 1 M to about 5 M. It is application specific. The term "M" used denotes molar or moles per liter.

Normally, a slurry of finely ground calcium hydroxide suspended in water (about 50% of W/V) is the preferred way of introducing the calcium hydroxide, in increments, into the a stirring solution of sulfuric acid, with or without the presence of calcium sulfate. Ordinarily, the reaction is carried out below 40° C., preferably below room temperature, and more preferably below 10° C. The time to add calcium hydroxide can range from about 1 hour to about 4 hours. The agitation speed can vary from about 600 to about 700 rpm or higher. After the mixing, the mixture is filtered through a 5 micron filter. The filtrate is then allowed to sit overnight and the fine sediment is removed by decantation.

The calcium hydroxide used is usually FCC Grade of about 98% purity. For every mole of concentrated acid, such as sulfuric acid, the amount, in mole, of calcium hydroxide used is application specific and ranges from about 0.1 to about 1.

The optional calcium carbonate is normally FCC Grade having a purity of about 98%. When used with calcium hydroxide as described above, for every mole of concentrated acid, such as sulfuric acid, the amount, in mole, of calcium carbonate ranges from about 0.001 to about 0.2, depending on the amount of calcium hydroxide used.

The optional carbon dioxide is usually bubbled into the slurry containing calcium hydroxide at a speed of from about 1 to about 3 pounds pressure. The carbon dioxide is bubbled into the slurry for a period of from about 1 to about 3 hours. The slurry is then added to the reaction vessel containing the concentrated sulfuric acid.

Another optional ingredient is calcium sulfate, a Group IIA salt of a dibasic acid. Normally, dihydrated calcium sulfate is used. As used in this application, the phrase "calcium sulfate," or the formula "$CaSO_4$," means either anhydrous or hydrated calcium sulfate. The purity of calcium sulfate (dihydrate) used is usually 95–98% FCC Grade. The amount of calcium sulfate, in moles per liter of concentrated sulfuric acid ranges from about 0.005 to about 0.15, preferably from about 0.007 to about 0.07, and more preferably from about 0.007 to about 0.04. It is application specific.

From experimental data, a slope was generated showing the ratio of calcium hydroxide to concentrated sulfuric needed for a desired final acid normality of AGIIS. See, FIG. 1.

The slope in FIG. 1 was created from two pairs of data points found by titrating a given amount of acid to a desired final acid normality. The accuracies were determined chemically. The final acid normality of the finished product ranges from about 1.2 to about 29. To produce one liter of 1.2 N AGIIS, it was found that for every mole of concentrated sulfuric acid, 0.45 moles of $Ca(OH)_2$ was required. To produce one liter of 27 N AGIIS, it was found that for every mole of concentrated sulfuric acid, 0.12 moles of $Ca(OH)_2$ was required. The data were then plotted onto a graph where the Y-axis represents final acid normality and the X-axis represents moles of $Ca(OH)_2$/1 mole of concentrated sulfuric acid, where $X_1=0.45$, $X_2=0.12$, $Y_1=1.2$, and $Y_2=27$. The slope of the line was found by using the equation $(Y_1-Y_2)/(X_1-X_2)$, which was $-78.18$. The line can be represented by the equation $Y=mX+b$, where $mX$ is the slope, and b is the Y intercept. The highest acid normality was 36.65, thus the equation is:

$$Y=-78.18X+36.65$$

This slope is useful for the preparation of an AGIIS solution having a desired final acid normality.

Broadly, the method of preparing AGIIS having a desired final acid normality involves the steps given below. The calculations are based on a 1 liter of final volume of AGIIS, the amounts of acid (concentrated sulfuric acid) and base (calcium hydroxide) are in moles, the ratio of base to acid is the number of moles of base (calcium hydroxide) for every mole of acid (concentrated sulfuric acid). The steps are:

(a) Determining the amount of mineral acid (such as concentrated sulfuric acid), in moles, needed to produce AGIIS having the desired final acid normality ("N") by using a relationship given by the following equation:

$$E_1=(N/2)+(N/2^{+B})$$

in which $E_1$ is the amount of acid, in moles, required before correcting for purity, or purity adjustment; N is the desired final acid normality; and B is the mole ratio of the Group IIA hydroxide to the mineral acid needed to obtain the AGTIIS having N, and B is derived from a pre-plotted curve depicting the relationship of the mineral acid and the Group IIA hydroxide for a desired final N;

(b) making purity adjustment for the mineral acid used. The correction for the purity of the acid used is accomplished by the equation:

$$E_2=E_1/C$$

in which $E_2$ is the amount of acid, in moles, required after correcting for purity of the acid used, or purity adjustment; $E_1$ is as defined above; and C is purity adjustment factor for the acid used. For concentrated sulfuric acid, the average acid strength is about 96.5%, and thus C is 0.965;

(c) determining the amount of water, in ml, that has to be added to the acid whose acid solution will then, after the reaction, give the desired final acid normality N. The relationship is as follows:

$$G=J-E_2-I$$

in which G is the amount of water required to be added to the mineral acid solution to get the desired final acid normality; J is the final volume of the aqueous mineral acid solution; I is the volume amount of Group IIA hydroxide needed (see, below); and $E_2$ is as defined above;

(d) adding G to $E_2$ to give the final aqueous solution of the mineral acid, in which both G and $E_2$ are as defined above;

(e) determining the amount of base, (such as calcium hydroxide), in moles, needed for the reaction to produce AGIIS having the desired final acid normality N. For example, from the straight line in FIG. 1, the mole ratio of $Ca(OH)_2$ to concentrated $H_2SO_4$ to achieve a certain final acid normality can be determined.

the amount of the base, in moles, needed is:

$$F_1=N/2 \times B$$

in which $F_1$ is the amount of base, in moles, needed; and N and B are as defined above;

(f) the correction for the purity of the base used is accomplished by the equation:

$$F_2=F_1/D$$

in which $F_2$ is the amount of base, in moles, required after correcting for purity of the base used, or purity adjustment; and D is purity adjustment factor for the base used.

The average purity of sodium hydroxide is about 98%, and, thus, D, in this case, is 0.98;

(g) determining the amount of water, in ml, needed to make the slurry of base. The relationship is as follows:

$$H=F_2 \times 1.5$$

in which H is the volume of water, in ml, needed to make the slurry of base which, in turn, will give AGIIS with the desired final acid normality N. $F_2$ is as defined above. The H given is an approximation and should be adjusted to a desired final weight volume. Thus, for example, 50 g of base should be adjusted to a final volume of 100 ml because the slurry used is a 50:50 mixture of solid and water;

(h) determining the volume, in ml, of the base slurry or solution to be added to the acid solution to give AGIIS with the desired final acid normality N. The relationship can be expressed as:

$$I=F_2 \times 2$$

in which I is the volume, in ml, of the slurry or solution of base to be added to the acid solution; and $F_2$ is as defined above;

(i) adding H to $F_2$ to give the final aqueous slurry or solution of the base, in which both H and $F_2$ are as defined above;

(j) adding the final aqueous solution or slurry or the base of (i) to the final aqueous solution of mineral acid of (d);

(k) allowing the final aqueous solution or slurry of the base and the final aqueous solution of mineral acid (j) to react; and (l) removing solid formed from the reaction of (k).

In the event that $CaSO_4$ is used for the reaction by adding it to the solution of concentrated $H_2SO_4$, the amount of $CaSO_4$, in grams per liter of solution based on final volume, has the following relationship:

| | |
|---|---|
| 1–5 | 5 |
| 6–10 | 4 |
| 11–15 | 3 |
| 16–20 | 2 |
| 21–36 | 1 |

The AGIIS obtained could have an acid normality range of from about 0.05 to about 31; the pH of lower than 0; boiling point of from about 100 to about 106° C.; freezing point of from about −8° C. to about 0°C.

AGIIS obtained from using the reaction of $H_2SO_4$/Ca $(OH)_2$/$CaSO_4$ had the following analyses (average):

AGIIS with Final Acid Normality of 1.2 N, pH of −0.08

$H_3O^+$, 2.22%; Ca, 602 ppm; $SO_4$, 73560 ppm; K, 1.36 ppb; impurities of 19.68 ppm, and neither Na nor Mg was detected.

AGIIS with Final Acid Normality of about 29 N pH of about −1.46

$H_3O^+$, 30.68%; Ca, 52.9 ppm; $SO_4$, 7356000 ppm; K, 38.02 ppb; and neither Na nor Mg was detected.

Besides concentrated sulfuric acid, other polyprotic acids, such as phosphoric acid, phosphorous acid, chloric acid, iodic acid, or others can be used.

Likewise, aqueous solutions of other alkalines or bases, such as Group IA hydroxide solution or slurry and Group IIA hydroxide solution or slurry can be used. Groups IA and IIA refer to the two Groups in the periodical table. The use of Group IIA hydroxide is preferred. Preferably, the salts formed from using Group IIA hydroxides in the reaction are sparingly-soluble in water. It is also preferable to use only Group IIA hydroxide as the base without the addition of Group IA hydroxide.

After the reaction, the resultant concentrated acidic solution with a relatively low pH value, typically below pH 1, can then be diluted with de-ionized water to the desired pH value, such as pH of about 1 or about 1.8.

However, it is sometimes desirable not to prepare a very concentrated AGIIS solution and then dilute it serially to obtain the solution having the desired final acid normality. It is often desirable to prepare a solution of AGIIS having a desired final pre-determined acid normality according to the method described in this application so that not much dilution of the product is required before use.

As discussed above, AGIIS has relatively less dehydrating properties (such as charring sucrose) as compared to the saturated solution of $CaSO_4$ in the same concentration of $H_2SO_4$. Further, the stability and non-corrosive nature of the AGIIS of the present invention can be illustrated by the fact that a person can put his or her hand into this solution with a pH of less than 0.5 and, yet, his or her hand suffers no irritation, and no injury. If, on the other hand, one places his or her hand into a solution of sulfuric acid Of pH of less than 0.5, an irritation would occur within a relatively short span of time. A solution of 28 N of sulfuric acid saturated with calcium sulfate will cause chemical burn to a human skin after a few seconds of contact. In contrast, AGIIS solution of the same normality would not cause chemical burn to a human skin even after in contact for 5 minutes. The AGIIS of the present invention does not seem to be corrosive when being brought in contact with the environmental protective covering of plants (cuticle) and animals (skin). AGIIS is non-volatile at room temperature. Even as concentrated as 29 N, the AGIIS has no odor, does not give off fumes in the air, and is not irritating to a human nose when one smells this concentrated solution.

The "additive" of the present invention appears to enhance, and also appears to be synergistic to, the effectiveness of the AGIIS. Examples of the additive include alcohol, organic acid, periodic acid, and surfactant. The amount of additive added to the AGIIS varies depending on the desired final weight percent of the additive in the final adduct composition. The weight percent of additive needed for the adduct composition of the present invention can vary from about 0.01 to about 99.99, based on the total weight of the final adduct composition. In one aspect, if the additive is to be added to the concentrated AGIIS with a very low pH value, then the amount of the additive added has to be adjusted in anticipation of further dilution with water to raise the pH value of the final adduct composition. The alcohol additive preferred for the present invention includes methanol, ethanol, propanol, i-propanol, and other lower alkyl alcohols.

Organic acid additive of the present invention includes carboxylic acid. A carboxylic acid is an organic compound containing the —COOH group, i.e., a carbonyl attached to a hydroxyl group. Preferred organic acids for the present invention include lactic acid, acetic acid, propionic acid, oxalic acid, and per-acetic acid.

A surfactant for the present invention is a surface-active agent. It is usually an organic compound consisting of two parts: One, a hydrophobic portion, usually including a long hydrocarbon chain; and two, a hydrophilic portion which renders the compound sufficiently soluble or dispersible in water or another polar solvent. Surfactants are usually classified into: (1) an-ionic, where the hydrophilic moiety of the molecule carries a negative charge; (2) cat-ionic, where this moiety of the molecule carries a positive charge; and (3) non-ionic, which do not dissociate, but commonly derive their hydrophilic moiety from polyhydroxy or polyethoxy structures. Other surfactants include ampholytic and zwitterionic surfactants. A preferred surfactant for the present invention includes polysorbates (Tween 80).

Unless otherwise defined, the amount of each ingredient or component of the present invention is based on the weight percent of the final composition, usually the concentrate before further dilution to achieve the desired pH of about 1.8. The AGIIS having a pH of about 1.8 is usually further diluted with water before applying to an animal product or a plant product.

One way of preparing a concentrate of the AGIIS having an ethanol additive and a lactic acid additive is by mixing with stirring at ambient temperature 634 mL of 200 proof FCC ethanol (16.5 weight %); 75 mL. of 85% lactic acid (1.9 weight %); 1536 mL of a solution of AGIIS having a pH of about 0.2–0.4 (40 weight %); and 1595 mL of de-ionized water (41.5 weight %). The resultant concentrate of AGIIS with two additives showed a pH of about 1.65–1.8.

One way of preparing a concentrate of the AGIIS having ethanol, lactic, and Tween 80 additives is by mixing with stirring at ambient temperature 634 mL of 200 proof FCC ethanol (16.5 weight %); 75 mL. of 85% lactic acid (1.9 weight %); 1920 mL of a solution of AGIIS having a pH of about 0.2–0.4 (50 weight %); 255 mL of Tween 80 (6.6 weight %); and 957.6 mL of de-ionized water (25 weight %). The resultant concentrate of AGIIS with three additives showed a pH of about 1.45–1.7.

A "biological contaminant" is defined as a biological organism, or the product of biological organism, such as toxin, all of which contaminate the environment and useful products. This biological contaminant results in making the environment or product hazardous.

Biological contaminants, such as bacteria, fungi, mold, mildew, spores, and viruses have potentially reactive substances in their cell wall/membranes; however, they hide in cells (viruses and some bacteria)and/or secrete biofilms (most bacteria, fungi, mold and mildew) to protect them from the environment.

Bacterial form or elaborate intracellular or extracellular toxins. Toxin is a noxious or poisonous substance that: (1) is an integral part of the bacteria; (2) is an extracellular product (exotoxin) of the bacteria; or (3) represents a combination or the two situations, formed or elaborated during the metabolism and growth of bacteria. Toxins are, in general, relatively complex antigenic molecules and the chemical compositions are usually not known. The harmful effects of bacteria come not only from the bacteria themselves, but also from the toxins produced by bacteria. Toxins produced by bacteria are just as, if not more, hazardous to the product than the bacteria themselves. ordinary disinfectants, such as quaternary ammonium compounds, will kill bacteria but have no effect on bacterial toxins and endotoxins. In fact, many disinfectants actually contribute to the endotoxins problems by causing their release from the bacteria. The bacterial toxins and endotoxins can cause serious adverse effects in human and animals. Endotoxins are the major cause of contamination in food products, in the production of pharmaceuticals, medical devices, and other medical products. Thus, while "decontaminating" a product infested with bacteria, it is not enough to simply kill or reduce the number of bacteria. To get a safe and decontaminated product, the toxins and endotoxins of the bacteria must also be destroyed. Neither killing the microorganism alone nor destroying the toxins alone is enough in the real world. To be useful, when reducing biological contaminants in a nutriment or in an equipment, the growth of biological organisms must be controlled and reduced, and, at the same time, the product of biological organisms (such as toxins) must be removed and/or destroyed.

The outer covering, i.e. epidermis, of animals and cuticle of plants resist the growth and/or entry of the above microorganisms into the interior of the complex organism. One of the microbial growth prevention methods used by plants and animals is the maintenance of a surface pH or secretion of a coating that is not conducive to the attachment and propagation of micro-organisms. After a plant product is harvested or an animal product processed, these products loose the ability to resist the infestation of micro-organisms. By spraying the composition of the present invention plus defined additives on fruits, vegetables, and whole plants post harvest or washing or packing animal products in the composition, the growth and propagation of micro-organisms in these products can be reduced. If plant or animal products are packed in the composition an additional benefit is realized when the product is heated because the pH of the composition, and in turn the product, goes down giving the added potential of the composition of destroying any micro-organisms, their toxins or other harmful substances.

The composition of the present invention was found to be a "preservative." The composition is not corrosive; however, it can create an environment where destructive micro-organisms cannot live and propagate. The utility of this method of preservation is that additional chemicals do not have to be added to the food or other substance to be preserved because the inherent low pH of the mixture is preservative. Since preservative chemicals do not have to be added to the food substance, taste is improved and residues are avoided. Organoleptic testing of a number of freshly preserved and previously preserved food stuffs have revealed the addition of composition improves taste and eliminates preservative flavors. The term "organoleptic" means making an impression based upon senses of an organ or the whole organism. In another use, the composition was added to various food dressing, fresh juices and fermented beverages (wine). The resulting taste was unanimously judged better than the starting or control beverage. Use of the composition both as a preservative and taste enhancer for food and beverages will produce a safer and more desirable product. Additionally the composition can be added to biologics, pharmaceuticals and other preservative sensitive products to enhance their safety and extend shelf life. It can also be used as an ingredient to adjust product pH.

Conventional cleaning of biopharmaceutical and vaccine equipment is always problematical. Bioreactor vessels, where genetically altered yeast and bacteria produce biopharmaceutical products, are very sensitive to residues left during the cleaning process. The adduct or composition of the present invention is extremely useful in the primary cleaning of these vessels following production termination and for final cleaning and rinsing just prior to reestablishing the culture in the reactor vessel. The composition's ability to completely remove residues will insure the success of the culture and eliminate the possibility of contamination in the biopharmaceutical or vaccine product.

Another field of manufacturing where cleaning is critical is in the precision injection molding of plastic and composite materials for critical use parts in medical devices and other industrial products. The composition of the present invention can clean the injection molds quickly and efficiently between runs without damaging the molds or leaving residues which can cause defects in the product. Additionally, the composition could be used to remove excess materials from the parts and acid etch or clean parts prior to assembly and welding. The composition of the present invention is useful to clean the surface of non metallic parts to be chemically, heat or ultrasonically welded. If the device is wet packaged, i.e. suture material, then the composition can be used as a packaging preservative.

Agricultural applications for the composition of the present invention are of special interest. The ability to manipulate the pH of hydroponic plant production water will influence fruit production and disease control. Synchronization of harvest and completeness of harvest can be aided by the composition. Olive, nut and some fruit trees are harvested by mechanical shaking. This shaking procedure must occur several times because the fruit and stem do not always ripen at the same time. Spraying the tree with the composition prior to harvest activities can cause the stems and produce to mature rapidly. Only one or two shaking procedures will be required to completely harvest the produce, thus reducing harvest cost and damage to the trees.

Bacteria, fungus, yeast and molds can reduce plant yields or effect the quality of crops near, at, or post harvest. The composition of the present invention can be useful in preventing mold and mildew when crops in production are subjected to wet conditions. This is especially true in corn, maize and other grain sorghram production. Grapes destined for raisin production are harvested and left to dry in the field on paper or cloth tarps between the vines. If wet weather persists the raisins will mold during the drying process resulting in an unusable product. Spraying the composition on the grapes prior to harvest, dipping the clusters during harvest, treating the tarps, spraying the drying clusters, and washing the raisins prior to packing will result in raisins free of mold. The same methods can be used to assure uniformity of grapes during wine making. The composition of the present invention can be used to control pH and adjust taste of wine and other fermented beverages.

The same use of the composition of the present invention can be made when storing grains. Mold, mildew and other fungal infestations of stored grains produce mycotoxins. These mycotoxins are very harmful to animals that consume contaminated grains. Mycotoxin intoxication results in organ damage, decreased production, or death. Chemicals containing mercury and iodine are used to preserve planting seed, but there are no preservatives for grains destined for food or feed which do not leave harmful residues. Grains at harvest, during processing or in storage could be exposed to the composition, with or without additives, to create an environment where these organisms would not grow on the grain or in the storage container.

Specific field applications for military use are numerous. The primary application is in the decontamination of drinking water. Current methods for individual drinking water decontamination consist of placing iodine tablets into a canteen of water and waiting a period of time. If a small amount of the composition of the present invention is added to the water, time for disinfection would be significantly reduced and there would be no need for iodine tablets. Additional applications for field living would include field waste decontamination, cooking liquid for food sources of questionable sanitary status, first aid irrigation solution for wounds and decontamination, dilution and clean up of toxic or dangerous substance spills, and equipment cleaning and decontamination. This is especially important when food service under field conditions does not always allow for hot water cleaning of equipment.

A biological contaminant is defined as a biological organism, or the product of biological organism, or both, each of which contaminates the environment and useful products. This biological contaminant results in making the environment or product hazardous.

Bacteria, fungi, mold, mildew, and viruses have potentially reactive substances in their cell wall/membranes; however, they hide in cells (viruses and some bacteria)and/ or secrete biofilms (most bacteria, fungi, mold and mildew) to protect them from the environment.

The outer covering, i.e. epidermis, of animals and cuticle of plants resist the growth and/or entry of the above micro-organisms into the interior of the complex organism. One of the microbial growth prevention methods used by plants and animals is the maintenance of a surface pH or secretion of a coating that is not conducive to the attachment and propagation of micro-organisms. After a plant product is harvested or an animal product processed, these products loose the ability to resist the infestation of micro-organisms. By spraying the AGIIS plus defined additives on fruits, vegetables, and whole plants post harvest or washing or packing animal products in the composition, the growth and propagation of micro-organisms in these products can be reduced. If plant or animal products are packed in the composition an additional benefit is realized when the product is heated because the pH of the composition, and in turn the product, goes down giving the added potential of the composition of destroying any micro-organisms, their toxins or other harmful substances.

The composition of the present invention was found to be a "preservative." The composition is not corrosive; however, it can create an environment where destructive micro-organisms cannot live and propagate, thus prolong the shelf-life of the product. The utility of this method of preservation is that additional chemicals do not have to be added to the food or other substance to be preserved because the inherent low pH of the mixture is preservative. Since preservative chemicals do not have to be added to the food substance, taste is improved and residues are avoided. Organoleptic testing of a number of freshly preserved and previously preserved food stuffs have revealed the addition of composition improves taste and eliminates preservative flavors. Organoleptic means making an impression based upon senses of an organ or the whole organism. In another use the composition was added to various fresh juices and fermented beverages (wine). The resulting taste was unanimously judged better than the starting or control beverage. Use of the composition both as a preservative and taste enhancer for food and beverages will produce a safer and more desirable product. Additionally the composition can be added to biologics, pharmaceuticals and other preservative sensitive products to enhance their safety and extend shelf life. It can also be used as an ingredient to adjust product pH.

Some biofilms are resistant to the AGIIS; however, this resistance can be overcome by adding small amounts of polar organic molecules namely, the additive to the AGIIS. Molecules such as ethyl alcohol, lactic acid and surfactants (such as polysorbate 80, (Tween 80) can enhance the activity of the composition as well as increase the speed and efficacy of the antimicrobial properties of the composition.

In the composition of the present invention, the addition of one, two or all of the above mentioned classes of additives, to the aqueous solution of AGIIS appear to enhance the penetration or the contact of reactive surface between the composition and the cleaning target. Broadly, one embodiment of the present invention is a combination of the aqueous solution of AGIIS with ethyl alcohol, lactic acid, and polysorbate 80, also known as Tween 80. This combination not only cleans a surface of organic or inorganic residues, but kills up to $10^8$ organisms. Another combination, when applied with heat, will remove bacterial endotoxins from glass, metal and plastic surfaces without damaging these surfaces. This capability lends the combinations to be useful in the cleaning of pharmaceutical or biological processing and manufacturing equipment "in place." This capability does not require the dismantling of this expensive equipment for cleaning. Reduction of endotoxins on processing equipment and primary packaging of vaccines and pharmaceutical products is a requirement for safe use of drugs and vaccines.

Conventional cleaning of biopharmaceutical and vaccine equipment is always problematical. Bioreactor vessels, where genetically altered yeast and bacteria produce biopharmaceutical products, are very sensitive to residues left during the cleaning process. The adduct or composition of the present invention is extremely useful in the primary cleaning of these vessels following production termination and for final cleaning and rinsing just prior to reestablishing the culture in the reactor vessel. The composition's ability to completely remove residues will insure the success of the culture and eliminate the possibility of contamination in the biopharmaceutical or vaccine product.

Another field of manufacturing where cleaning is critical is in the precision injection molding of plastic and composite materials for critical use parts in medical devices and other industrial products. The composition of the present invention can clean the injection molds quickly and efficiently between runs without damaging the molds or leaving residues which can cause defects in the product. Additionally, the composition could be used to remove excess materials from the parts and acid etch or clean parts prior to assembly and welding. The composition of the present invention is useful to clean the surface of non metallic parts to be chemically, heat or ultrasonically welded. Also, the adduct of the present invention is useful to remove excess adhesive materials and generally decontaminate the medical device prior to packaging. If the device is wet packaged, i.e. suture material, then the composition can be used as a packaging preservative.

Agricultural applications for the adduct or composition of the present invention are of special interest. The ability to manipulate the pH of hydroponic plant production water will influence fruit production and disease control. Synchronization of harvest and completeness of harvest can be aided by the composition. Olive, nut and some fruit trees are harvested by mechanical shaking. This shaking procedure must occur several times because the fruit and stem do not always ripen at the same time. Spraying the tree with the composition prior to harvest activities can cause the stems and produce to mature rapidly. Only one or two shaking procedures will be required to completely harvest the produce, thus reducing harvest cost and damage to the trees.

Bacteria, fungus, yeast and molds can reduce plant yields or effect the quality of crops near, at, or post harvest. The adduct or the composition of the present invention can be useful in preventing mold and mildew when crops in production are subjected to wet conditions. This is especially true in corn, maize and other grain sorghram production. Grapes destined for raisin production are harvested and left to dry in the field on paper or cloth tarps between the vines. If wet weather persists the raisins will mold during the drying process resulting in an unusable product. Spraying the composition on the grapes prior to harvest, dipping the clusters during harvest, treating the tarps, spraying the drying clusters, and washing the raisins prior to packing will result in raisins free of mold. The same methods can be used to assure uniformity of grapes during wine making. The composition of the present invention can be used to control pH and adjust taste of wine and other fermented beverages.

The same use of the composition of the present invention can be made when storing grains. Mold, mildew and other fungal infestations of stored grains produce mycotoxins. These mycotoxins are very harmful to animals that consume contaminated grains. Mycotoxin intoxication results in organ damage, decreased production, or death. Chemicals containing mercury and iodine are used to preserve planting seed, but there are no preservatives for grains destined for food or feed which do not leave harmful residues. Grains at harvest, during processing or in storage could be exposed to the composition, with or without additives, to create an environment where these organisms would not grow on the grain or in the storage container.

Specific field applications for military use are numerous. The primary application is in the decontamination of drinking water. Current methods for individual drinking water decontamination consist of placing iodine tablets into a canteen of water and waiting a period of time. If a small amount of the adduct or the composition of the present invention is added to the water, time for disinfection would be significantly reduced and there would be no need for iodine tablets. Additional applications for field living would include field waste decontamination, cooking liquid for food sources of questionable sanitary status, first aid irrigation solution for wounds and decontamination, dilution and clean up of toxic or dangerous substance spills, and equipment cleaning and decontamination. This is especially important when food service under field conditions does not always allow for hot water cleaning of equipment.

The following examples are provided to further illustrate this invention and the manner in which it may be carried out. It will be understood, however, that the specific details given in the examples have been chosen for purposes of illustration only and not be construed as limiting the invention. Unless otherwise defined, the amount of each ingredient or component of the present invention is based on the weight percent of the final composition.

EXAMPLE 1

AGIIS having an acid normality of 1.2 to 1.5 was prepared by the method of $H_2SO_4/Ca(OH)_2$.

An amount of 1055 ml (19.2 moles, after purity adjustment and taking into account the amount of acid neutralized by base) of concentrated sulfuric acid (FCC Grade, 95–98% purity) was slowly added with stirring, to 16.868 L of RO/DI water in each of reaction flasks a, b, c, e, and f. The amount of water had been adjusted to allow for the volume of acid and the calcium hydroxide slurry. The mixture in each flask was mixed thoroughly. Each of the reaction flasks was chilled in an ice bath and the temperature of the mixture in the reaction flask was about 8–12° C. The mixture was continuously stirred at a rate of about 700 rpm.

Separately, a slurry was made by adding RO/DI water to 4 kg of calcium hydroxide (FCC Grace, 98% purity) making a final volume of 8 L. The mole ratio of calcium hydroxide to concentrated sulfuric acid was determined to be 0.45 to 1 from FIG. 1. The slurry was a 50% (W/V) mixture of calcium hydroxide in water. The slurry was mixed well with a high-shear-force mixer until the slurry appeared uniform. The slurry was then chilled to about 8–12° C. in an ice bath and continuous stirred at about 700 rpm.

To each of the reaction flasks was added 150 ml of the calcium hydroxide slurry every 20 minutes until 1.276 L (i.e. 638 g dry weight, 8.61 moles, of calcium hydroxide) of the slurry had been added to each reaction vessel. The addition was again accompanied by well mixing at about 700 rpm.

After the completion of the addition of the calcium hydroxide to the reaction mixture in each reaction vessel, the mixture was filtered through a 5-micron filter.

The filtrate was allowed to sit for 12 hours, the clear solution was decanted to discard any precipitate formed. The resulting product was AGIIS having an acid normality of 1.2–1.5.

EXAMPLE 2

AGIIS having an acid normality of 2 was prepared by the method of $H_2SO_4/Ca(OH)_2/CaSO_4$.

For the preparation of 1 L of 2 N AGIIS, an amount of 79.54 ml (1.44 moles, after purity adjustment and taking into account the amount of acid to be neutralized by base) of concentrated sulfuric acid (FCC Grade, 95–98% purity) was slowly added, with stirring, to 853.93 ml of RO/DI water in a 2 L reaction flask. Five gram of calcium sulfate (FCC Grade, 95% purity) was then added slowly and with stirring to the reaction flask. The mixture was mixed thoroughly. At the point, the mixture would usually indicated an acid normality of 2.88. The reaction flask was chilled in an ice bath and the temperature of the mixture in the reaction flask was about 8–12° C. The mixture was continuously stirred at a rate of about 700 rpm.

Separately, a slurry was made by adding 49.89 ml of RO/DI water to 33.26 g (0.44 mole, after purity adjustment) of calcium hydroxide (FCC Grace, 98% purity) making a final volume of 66.53 ml. The mole ratio of calcium hydroxide to concentrated sulfuric acid was determined to be 0.44 to 1 from FIG. 1. The slurry was mixed well with a high-shear-force mixer until the slurry appeared uniform. The slurry was then chilled to about 8–12° C. in an ice bath and continuous stirred at about 700 rpm.

The slurry was then slowly added over a period of 2–3 hours to the mixture, still chilled in an ice bath and being stirred at about 700 rpm.

After the completion of the addition of slurry to the mixture, the product was filtered through a 5-micron filter. It was normal to observe a 20% loss in volume of the mixture due to the retention of the solution by the salt and removal of the salt.

The filtrate was allow to sit for 12 hours, the clear solution was decanted to discard any precipitate formed. The resulting product was AGIIS having an acid normality of 2.

EXAMPLE 3

AGIIS having an acid normality of 12 was prepared by the method of $H_2SO_4/Ca(OH)_2/CaSO_4$.

For the preparation of 1 L of 12 N AGIIS, an amount of 434.17 ml (7.86 moles, after purity adjustment and taking into account amount of acid neutralized by base) of concentrated sulfuric acid (FCC Grade, 95–98% purity) was slowly added, with stirring, to 284.60 ml of RO/DI water in a 2 L reaction flask. Three gram of calcium sulfate (FCC Grade, 95% purity) was then added slowly and with stirring to the reaction flask. The mixture was mixed thoroughly. The reaction flask was chilled in an ice bath and the temperature of the mixture in the reaction flask was about 8–12° C. The mixture was continuously stirred at a rate of about 700 rpm.

Separately, a slurry was made by adding 210.92 ml of RO/DI water to 140.61 g (1.86 moles, after purity adjustment) of calcium hydroxide (FCC Grace, 98% purity) making a final volume of 281.23 ml. The mole ratio of calcium hydroxide to concentrated sulfuric acid was determined to be 0.31 from FIG. 1. The slurry was mixed well with a high-shear-force mixer until the slurry appeared uniform. The slurry was then chilled to about 8–12° C. in an ice bath and continuous stirred at about 700 rpm.

The slurry was then slowly added over a period of 2–3 hours to the mixture, still chilled in an ice bath and being stirred at about 700 rpm.

After the completion of the addition of slurry to the mixture, the product was filtered through a 5-micron filter. It was normal to observe a 20% loss in volume of the mixture due to the retention of the solution by the salt and removal of the salt.

The filtrate was allow to sit for 12 hours, the clear solution was decanted to discard any precipitate formed. The resulting product was AGIIS having an acid normality of 2.

EXAMPLE 4

Test to determine if a pH 1.8 solution comprised of AGIIS and two additives (lactic acid and ethanol) could reduce contamination of alfalfa sprout seeds inoculated with *E. coli* 0157:H7.

A pH 1.8 solution comprised of AGIIS mixed with 0.05% lactic acid and 0.5% ethanol, was used to decontaminate alfalfa sprout seeds inoculated with $1.1 \times 10^{13}$ colony forming unit ("CFU") of *E. coli* 0157:H7 at 35° C., 40° C. and 45° C., respectively.

Treatment with the adduct comprising AGIIS and the additives combination defined above at 35° C. reduced the level of *E. coli* 0157:H7 contamination by >6 logs. Treatment at 40° C. did not significantly increase decontamination relative to that at 35° C. However, treatment at 45° C. decreased contamination by >8 logs, a significant difference.

EXAMPLE 5

Experiment to determine if a pH 1.8 solution comprised of AGIIS and three additives (lactic acid, ethanol and Tween 80) could decontaminate alfalfa sprout seeds inocluated with *E. coli* 0157:H7.

A pH 1.8 solution comprised of AGIIS, 0.05% lactic acid, 0.5% ethanol and 0.2% Tween 80, was used to decontaminate alfalfa sprout seeds inoculated with $1.1 \times 10^{13}$ CFU of *E. coli* 0157:H7 at 35° C., 40° C. and 45° C., respectively.

Treatment with AGIIS and the additives combination defined above at 35° C. and 40° C. reduced the level of *E. coli* 0157:H7 contamination by >6 logs. However, treatment at 45° C. decreased contamination by >8 logs, a significant difference.

EXAMPLE 6

Experiment to determine if a pH 1.8 solution comprised of AGIIS and three additives (lactic acid, ethanol and Tween 80) could decontaminate alfalfa sprout seeds inoculated with Salmonella spp.

A pH 1.8 solution comprised of AGIIS, 0.05% lactic acid, 0.5% ethanol and 0.2% Tween 80, was used to decontaminate alfalfa sprout seeds inoculated with $1.1 \times 10^{13}$ CFU of Salmonella spp, at 35° C., 40° C. and 45° C., respectively.

Treatment with AGIIS and the additives combination defined above at 35° C. and 40° C. reduced the level of Salmonella spp, contamination by >3 logs. However, treatment at 45° C. decreased contamination by >4 logs, a significant difference.

EXAMPLE 7

Study to assess the effect of treatment at different temperatures and with a pH 1.8 solution comprised of AGIIS, 0.5% ethanol, 0.05% lactic acid and 0.2% Tween 80 on the level of aerobic microbes associated with alfalfa sprouts (produce) prior to final packaging.

It was demonstrated that the number of CFU per gram of sprouts was reduced by 99.99% when they were treated with a pH 1.8 solution comprised of AGIIS, 0.5% ethanol, 0.05% lactic acid and 0.2% Tween 80 at ~25° C. for 15 min. From an organoleptic perspective there was no apparent effect on the sprouts. However, sprouts treated at 40° C. appeared limp, and were not as visually appealing as sprouts treated at room temperature.

EXAMPLE 8

Study to assess the effect of treatment at different temperatures and with a pH 1.8 solution comprised of AGIIS, 0.5% ethanol, 0.05% lactic acid and 0.2% Tween 80 on the shelf life of alfalfa sprouts held at 25° C.

Treatment at 40° C. for 15 min. made the sprouts whiter and cleaner looking, but the sprouts could not withstand the elevated temperature and degraded very fast. All samples within 36 hours were wilted and it was subsequently demonstrated that the Tween 80 additive adversely effected the organoleptic properties of alfalfa sprouts.

EXAMPLE 9

Effect of the addition of a pH 1.8 solution comprised of AGIIS, 0.5% ethanol, 0.05% lactic acid and 0.2% Tween 80 on the microflora of ground beef.

The object of the study was to determine if a pH 1.8 solution comprised of AGIIS, 0.05% lactic acid, 0.5% ethanol and 0.2% Tween 80 mixed with ground beef (hamburger) could reduce and/or control the level of meat associated microflora.

No difference in the organoleptic properties of the treated and untreated hamburger could be discerned. However, when meat specimens were stomached and the microbe level of each specimen was determined, it was shown that meat treated with the AGIIS/additive solution had an associated microbe population 50% lower than that of saline treated meat. Thus, it was concluded that the AGIIS/additive solution could reduce the level of microbe contamination and extend the shelf life of treated meat.

EXAMPLE 10

Study to assess the ability of treatment at 45° C. with a pH 1.4 solution comprised of AGIIS, 0.05% lactic acid, 0.5% ethanol, and 0.2% Tween 80 to reduce mold/fungal contamination and growth on raisins.

It was demonstrated that treatment reduced the amount of mold/fungal contamination associated with the raisins and appeared to suppress further growth. From an organoleptic perspective treatment removed significantly more dirt and debris than washing with water and the treated raisins were more appealing in that they appeared darker and fresher.

EXAMPLE 11

Effect of treatment 45° C. with a pH 1.4 solution comprised of AGIIS, 0.05% lactic acid, 0.5% ethanol, and 0.2% Tween 80 on the viability of *E. coli* 0157:H7 organisms.

*E coli* 0157:H7 organisms $1 \times 10^7$ were treated with the pH 1.4 solution comprised of AGIIS, 0.05% lactic acid, 0.5% ethanol, and 0.2% Tween 80 at 45° C. Serial dilutions of the treated material were plated to determine the effect of the treatment on the viability of the *E. coli* 0157:H7 organisms. The treatment killed 100% of the organisms, i.e., the CFU/ml was reduced from $1 \times 10^7$ to zero.

EXAMPLE 12

Study to assess the effect of treatment with solutions comprised of AGIIS, 0.5% ethanol and 0.05% lactic acid having a pH ranging from 1.4–1.8 on the shelf life of alfalfa sprouts held at 25° C.

Sprouts were treated for 10 min. in the containers in which the sprouts were purchased. With respect to organoleptic properties after 12–16 hours the deionized water and non-treated sprouts had a distinct sour smell to them. It was concluded that adequate amounts of water were not removed from the sprouts, therefore, they degraded quickly. It was further noted that Tween 80 was a negative factor in the extension of sprout shelf life. It was also observed that sprouts treated with pH 1.8 or lower were bleached. Despite the rotten and/or degraded appearance, sprouts treated with the prontonium solutions did not have a rotten sour smell.

EXAMPLE 13

Study to assess the effect of treatment with solutions comprised of AGIIS, 0.5% ethanol, 0.05% lactic acid and/or Tween 80 having a pH ranging from 1.4–1.8 on the shelf life of alfalfa sprouts held at 25° C.

Control sprouts and sprouts treated with deionized water did not appear as fresh as sprouts treated with the AGIIS. Control sprouts and sprouts treated with deionized water were browned and somewhat discolored, whereas AGIIS treated (30 seconds) sprouts looked fresher and whiter. After 24 hours sprouts treated with the lower pH AGIIS solutions (<1.8) exhibited excessive bleaching. At 48 hours post-treatment the control and deionized water treated sprouts were rotten and smelled badly (a lot of gas was produced by the samples). It was concluded that a pH 1.8 AGIIS containing solutions along with the additives ethanol (0.5%) and lactic acid (0.05%) were the most effective in extending shelf life. The sprouts looked as fresh as the day they were purchased 72 hr post-treatment at room temperature. Thus, pH 1.8 solutions containing AGIIS, and 0.5% ethanol and 0.05% lactic acid can extend the shelf life of the alfalfa sprouts.

EXAMPLE 14

Study to show that a pH 1.8 solution of AGIIS and 0.5% ethanol and 0.05% lactic acid kills *E. coli* used to contaminate sprout seed as opposed to physically removing the contaminants.

Seed samples (25 g each) were contaminated with either $1 \times 10^6$ or $1 \times 10^{13}$ *E. coli* 0157:H7 CFU. Seed samples were treated for 10 min with a pH 1.8 solution containing AGIIS and 0.5% ethanol and 0.05% lactic acid. A 1 mL aliquot of each seed suspension was removed and serially diluted following treatment. After plating each serial dilution the number of CFU associated with the seed were enumerated. Treatment reduced the number of organisms associated with the seeds by 4–5 logs. The bacteria are killed not just washed off.

EXAMPLE 15

Test to determine if treatment with a pH 1.8 solution of AGIIS, 0.5% ethanol, 0.05% lactic acid, and 0.2% Tween 80 could reduce and/or kill microbial organisms associated with the surface of tomatoes.

The normal level of microbial contaminates associated with the surface of tomatoes was shown to be $1 \times 10^6$. After treatment, a 3–4 log reduction in surface associated organisms was demonstrated. A 3–4 log reduction is sufficient to provide for an extended shelf life and reduce the probability of contamination of products made from tomatoes such as salsa.

EXAMPLE 16

Studies pertaining to the effect of treatment with a pH 1.8 solution of AGIIS, 0.5% ethanol, 0.05% lactic acid and 0.2% Tween 80 on microbial contamination and organoleptic properties.

One dozen chicken legs purchased from a local grocery were individually packaged and immersed for 10 min either in a pH 1.8 solution of AGIIS, 0.5% ethanol, 0.05% lactic acid and 0.2% Tween 80, or sterile saline (control). All chicken legs were then incubated at ambient room temperature for 24 hr.

The number of bacteria associated with drumsticks immersed in sterile saline after the 24 hr incubation period was ~$7 \times 10^{10}$ as compared to ~$6 \times 10^7$ for drumsticks treated with a pH 1.8 solution of AGIIS, 0.5% ethanol, 0.05% lactic acid and 0.2% Tween 80. With respect to the organoleptic properties, the drumsticks immersed in saline had a strong rotten smell after the 24 hr incubation period whereas the drumsticks treated with a pH 1.8 solution of AGIIS, 0.5% ethanol, 0.05% lactic acid and 0.2% Tween 80 exhibited a fresh smell not unlike that of the drumsticks when purchased. Moreover, treatment maintained the fresh appearance of the chicken.

It was therefore concluded that treatment with a pH 1.8 solution of AGIIS, 0.5% ethanol, 0.05% lactic acid and 0.2% Tween 80 could extend the shelf life of fresh meats, and in particular chicken.

EXAMPLE 17

Studies pertaining to the effect of treatment with a pH 1.8 solution of AGIIS, 0.5% ethanol, 0.05% lactic acid and 0.2%

Tween 80 on microbial contamination and organoleptic properties of shrimp.

Large headless shrimp purchased from a local grocery were packaged and immersed for 10 min either in a pH 1.8 solution of AGIIS, 0.5% ethanol, 0.05% lactic acid and 0.2% Tween 80 or sterile saline (control). All shrimp were then incubated at ambient room temperature for 24 hr. The number of bacteria associated with shrimp immersed in sterile saline after the 24 hr incubation period was ~$3.8 \times 10^{10}$ as compared to ~$1.4 \times 10^9$ for shrimp treated with a pH 1.8 solution of AGIIS, 0.5% ethanol, 0.05% lactic acid and 0.2% Tween 80. With respect to the organoleptic properties, the treated and untreated shrimp did not differ.

In another experiment, the shelf-life (freshness and physical appearance) of whole shrimp was found to have increased from about 0.75 day to 1.5 days at 25° C.

EXAMPLE 18

Investigation of the capacity of a pH 1.8 solution of AGIIS, 0.5% ethanol, 0.05% lactic acid and 0.2% Tween 80 to decontaminate chicken halves inoculated with *E. coli* 0157:H7.

Chicken halves inoculated with *E. coli* 0157:H7 were immersed in a pH 1.8 solution of AGIIS, 0.5% ethanol, 0.05% lactic acid and 0.2% Tween 80 or sterile saline for 10 min. After immersion the halves were placed in plastic bags with culture media and incubated at 37° C. for 2 hr. After the two hour incubation period the *E. coli* 0157:H7 titers were determined.

It was demonstrated that treatment with a pH 1.8 solution of AGIIS, 0.5% ethanol, 0.05% lactic acid and 0.2% Tween 80 reduced *E coli* 0157:H7 growth by ~1 log, i.e., from $1.5 \times 10^9$ to $1.2 \times 10^8$. No difference in organoleptic properties were noted.

EXAMPLE 19

Study to assess the ability of a pH 1.8 solution of AGIIS, 0.5% ethanol and 0.05% lactic acid to extend the shelf life of fruits and vegetables.
Berries
Blueberry, Raspberry and Grapes Treatment with a pH 1.8 solution of AGIIS, 0.5% ethanol and 0.05% lactic acid did not prevent multiplication of berry associated fungi but berries retained their shape and exhibited an overall better appearance.

Treatment had no effect on strawberries.
Whole Melons

Immersion of whole cantaloupe for 30 min in a pH 1.8 solution of AGIIS, 0.5w ethanol and 0.05% lactic acid slowed decay (observation made 48 hr post-treatment).
Cut Fruit Immersion of quarter sections of cantaloupe and honeydew melons in a pH 1.4 solution of AGIIS, 0.5% ethanol and 0.05% lactic acid suppress decay. The fruit treated with the pH 1.4 solution of AGIIS, 0.5% ethanol and 0.05% lactic acid refrigerated or kept at ambient room temperature retained their color and smelled fresh 24 hr later, whereas the fruit treated with sterile water had a rotten smell.
Cut Fruit Salad (Mixture of Apple, Pear, Peach and Melons)

Cut fruit salad treated with a pH 1.4 solution of AGIIS, 0.5% ethanol and 0.05% lactic acid had a fresh appearance 2 hours (room temperature) after treatment whereas fruit salad treated with water appeared brown and in the process of decay.
Cut Lettuce Cut lettuce treated with a pH 1.8 solution of AGIIS, 0.5% ethanol and 0. 05% lactic acid and incubated either at room temperature or at 40° C. had no effect with respect to decay at the edge of the leaves. However, the leaves of lettuce treated with the pH 1.8 solution of AGIIS, 0.5% ethanol and 0.05% lactic acid were intact after incubation for 6 days at room temperature, whereas the water treated leaves were slimy and had decayed to a rotten mass.
Tomatoes Cherry tomatoes treated with a pH 1.8 solution of AGIIS, 0.5% ethanol and 0.05% lactic acid or water exhibited no difference in appearance. However, as in a previous experiment tomatoes immersed in AGIIS exhibited a significantly extended shelf life.

EXAMPLE 20

The Ability of Adduct to clean Blueberry and Raspberry.

A combination composition, pH 1.4 solution of AGIIS, 0.5% ethyl alcohol and 0.05% lactic acid was applied to treat the berries by 15 minutes of immersion. A control group of berries treated in autoclaved Saline were performed parallel. Treated and non-treated berries were stomached with 1 ml/g saline. A comparison of plate-counts between treated and non-treated group were made. As both groups had a bacterial count number lower than $10^3$, it was concluded that the experiment is of no significance.

EXAMPLE 21

Study to determine if treatment with a pH 1.2 solution of AGIIS, 0.5% ethanol and 0.05% lactic acid can reduce microbial contamination of cut fruit.

The fruit of a cantaloupe and honeydew melon was cut into 1–1.5 inch cubes and inoculated for 10 min with $2.5 \times 10^9$ *E.coli* 0157:H7 organisms suspended in saline. After 10 min the melon cubes were treated with a pH 1.2 solution of AGIIS, 0.5% ethanol and 0.05% lactic acid or sterile saline by immersion for 10 min. After treatment melon cubes were stomached and the number of associated bacteria were determined. The number of *E. coli* 0157:H7 CFU associated with cantaloupe cubes was $7.2 \times 10^3$ as compared to $3.4 \times 10^5$ associated with saline treated cubes, i.e., treatment reduced the contamination level by ~98%. The number of *E. coli* 0157:H7 CFU associated with honeydew cubes was $5.3 \times 10^3$ as compared to $1.4 \times 10^5$ associated with saline treated cubes, i.e., treatment reduced the contamination level by ~95%.

EXAMPLE 22

Study to determine if treatment with a solution of AGIIS, ethanol and lactic acid can prevent oxidation of potatoes. Potatoes were peeled and immersed in a pH 1.4 solution of AGIIS, 0.5% ethanol, 0.05% lactic acid and 0.2% Tween 80 or in water for 15 min. After treatment potatoes were removed and incubated on an open shelf for 24 hrs at ambient room temperature. Water treated potatoes started turning black within 30 min. whereas potatoes treated with the AGIIS solution stayed white for several hours and a noticeable difference was evident 24 hr post-treatment.

EXAMPLE 23

A previously painted surface on a house built in 1895 was cleaned with a solution of AGIIS, pH 2, and 0.2% Tween-80 surfactant. All surface contamination was removed and was visually cleaner than a corresponding area cleaned with an ammonia cleaner. The cleaned surface was allowed to dry and a coat of acrylic paint was applied. One week later the paint appeared normal and had not bubbled or peeled.

EXAMPLE 24

A used driveway with oil stains was cleaned using AGIIS pH 2 and a 0.2% Tween-80 surfactant. Two identical areas were cleaned. The area treated with the AGIIS solution was whiter than the detergent only area and was judged cleaner by the observer.

EXAMPLE 25

A small area of a new concrete sidewalk was sprayed with pH 1.8 AGIIS and 0.05% lactic acid mixture. After the area was allowed to dry the sidewalk was sealed with a concrete sealant. The appearance of the area etched with the AGIIS was different from the surrounding concrete; however, the sealer was adhered to the concrete and was impervious to water.

EXAMPLE 26

A green pepper plant had 3 peppers on the plant at various stages of development. A mixture solution of pH 1.8 AGIIS and 0.5% lactic acid was sprayed on the plant every other day for 6 consecutive applications. The largest of the peppers began to immediately turn red. The smaller peppers increased in size rapidly, but began turning red after the third application. At the end of the treatments, the peppers were of different sizes, but uniformly red in color.

EXAMPLE 27

Potable water contained non-coliform organisms. A mixture of pH 1.4 AGIIS and 0.05% lactic acid was added to this water to bring the pH to 2.0. There was no growth when the water was cultured for organisms and the water could be consumed without adverse effects.

EXAMPLE 28

Test to determine if a pH 1.1 solution comprised of AGIIS, 0.5% ethanol and 0.05% lactic acid can destroy the viability of bacteria present in water collected from a street puddle. Water was collected from a puddle at the corner in front of a laboratory building. It was determined that the pH of the water was 7.4. Puddle water was titrated with a pH 1.1 solution comprised of AGIIS, 0.5% ethanol and 0.05% lactic acid or sterile saline and treated at ambient room temperature. Following treatment, an aliquot of the AGIIS and saline treated water was serially diluted and plated to determine the number of viable organisms. The pH 1.1 solution comprised of AGIIS, 0.5% ethanol and 0.05% lactic acid used to treat the water effectively decreased the number of viable organism relative to the control of saline.

EXAMPLE 29

Experiment to determine if a pH 1.56 solution comprised of AGIIS and three additives (lactic acid, ethanol and Tween 80) could decontaminate alfalfa sprout seeds inoculated with *Listeria monocytogenes*. A pH 1.56 solution comprised of AGIIS, 0.05% lactic acid, 0.5% ethanol and 0.2% Tween 80, was used to decontaminate alfalfa sprout seeds inoculated with *Listeria monocytogenes* at 45° C. Treatment with the adduct combination defined above at 45° C. reduced the level of *Listeria monocytogenes* contamination by >6 logs compared to sprout seeds inoculated with *Listeria monocytogenes* and treated with sterile saline.

EXAMPLE 30

The following protocol was used in this and the next three experiments.
1. Make a solution by adding concentrated AGIIS (Ca(OH)$_2$/H$_2$SO$_4$/CaSO$_4$ method)solution to deionized H$_2$O to adjust the pH to desired level, and then per-acetic acid was added.
2. Culture bacteria until just before they reach stationary phase.
3. Set out and label numerically sterile 15 ml Falcon tubes. Add 4 ml of solution prepared as described in step #1 to the first tube. Add 4 ml of sterile saline to all the rest of the tubes.
4. Set the timer to 60 seconds.
5. Add 1 ml of bacterial culture to first tube, start the timer.
6. After 60 sec has elapsed, immediately transfer 1 ml to the next tube. Vortex and transfer 1 ml to the next tube. Perform in succession to complete serial dilution.
7. Plate in triplicate by transferring 0.1 ml from each tube to three different culture plates. Incubate each plate overnight and count the number of colonies per plate 24 hr later to determine the number of survivors post-treatment.
8. To determine the number of bacteria subjected to treatment, make a serial dilution of original culture and plate in triplicate 0.1 ml from each dilution.

Tomatoes were contaminated with >1×10$^7$ CFU of salmonella by dipping the tomatoes in the bacteria and then letting them air dry. Treated tomatoes were immersed in a solution of an adduct containing AGIIS (pH 1.2, 0.063 N) mixed with 80 ppm of per-acetic acid for 1 min. After treatment the tomatoes were stomachered and an aliquot was plated to quantitate the number of associated organisms. In summary treatment with the adduct reduced the number of associated organisms by >4 logs.

EXAMPLE 31

Blueberries were contaminated with >1×10$^{10}$ CFU of salmonella by dipping the blueberries in the bacteria and then letting them air dry. Treated blueberries were immersed in a solution of an adduct containing AGIIS (pH 1.2, 0.063 N) mixed with 0.48 ml/L, or 80 ppm, of per-acetic acid for 1 min. After treatment the blueberries were stomachered and an aliquot was plated to quantitate the number of associated organisms. In summary treatment with the adduct reduced the number of associated organisms by >5 logs.

EXAMPLE 32

Apples were cut into quarters by cutting through the stem. The pieces were contaminated >1×10$^9$ CFU of salmonella by dipping the pieces in the bacteria and then letting them air dry. Treated apples were immersed in a solution of an adduct containing AGIIS (pH 1.2, 0.063 N) mixed with 0.48 ml/L, or 80 ppm, of per-acetic acid for 1 min. After treatment the apples were rinsed vigorously with saline and an aliquot of the rinse was plated to quantitate the number of associated organisms. In summary treatment with the adduct reduced the number of associated organisms by >8 logs.

EXAMPLE 33

Broccoli were contaminated with >1×10$^7$ CFU of salmonella by dipping the broccoli in the bacteria and then letting them air dry. Treated broccoli was immersed in a solution of an adduct containing AGIIS (pH 1.2, 0.063 N) mixed with 0.48 ml/L, or 80 ppm, of per-acetic acid for 1 min. After treatment the broccoli were stomachered and an aliquot was plated to quantitate the number of associated organisms. In summary treatment with the adduct reduced the number of associated organisms by >5 logs.

What is claimed is:

1. A method for preparing an adduct having a desired final acid normality, comprising:

(a) determining the amount of a mineral acid needed by the following equation:

$$E=(N/2)+(N/2+B)$$

wherein $E_1$ is the amount of the mineral acid, in moles, required before making purity adjustment; N is the desired final acid normality; and B is the mole ratio of a Group IIA hydroxide to the mineral acid needed to obtain a solution or suspension of an AGIIS having N, and B is derived from a pre-plotted curve depicting the relationship of the mineral acid and the Group IIA hydroxide for a desired N;

(b) making purity adjustment for the mineral acid used by the following equation:

$$E_2=E_1/C$$

wherein $E_2$ is the amount of the mineral acid, in moles, required after purity adjustment; $E_1$ is as defined above; and C is the purity adjustment factor for the mineral acid;

(c) determining the amount of water, in ml, needed to be added to the mineral acid by the following equation:

$$G=J-E_2-I$$

wherein G is the amount of water, in ml, required to be added to the mineral acid; J is the final volume of aqueous mineral acid solution; I is the volume amount of Group IIA hydroxide needed, given below; and $E_2$ is as defined above;

(d) adding G to $E_2$ to give the final aqueous solution of the mineral acid, wherein both G and $E_2$ are as defined above;

(e) determining the amount of Group IIA hydroxide, in moles, needed by the following equation:

$$F_1=N/2\times B$$

wherein $F_1$ is the amount of Group IIA hydroxide, in moles, needed before making purity adjustment; and B and N are as defined above;

(f) making purity adjustment for the Group IIA hydroxide used by the following equation:

$$F_2=F_1/D$$

wherein $F_2$ is the amount of the Group IIA hydroxide, in moles, required after purity adjustment; $F_1$ is as defined above; and D is the purity adjustment factor for the Group IIA hydroxide;

(g) determining the amount of water, in ml, needed to make the solution or slurry of Group IIA hydroxide by the following equation:

$$H=F_2\times 1.5$$

wherein H is the amount of water, in ml, needed to make the solution or slurry of Group IIA hydroxide; and $F_2$ is as defined above;

(h) determining the amount of the aqueous solution or slurry of Group IIA hydroxide, in ml, needed to be added to the aqeuous solution of mineral acid to give the solution or suspension of the AGIIS with a desired final acid normality by the following equation:

$$I=F_2\times 2$$

wherein I is the amount of Group IIA hydroxide solution or slurry, in ml, needed; and $F_2$ is as defined above;

(i) adding H to $F_2$ to give the final aqueous solution or slurry of Group IIA hydroxide, wherein both H and $F_2$ are as defined above;

(j) adding the final aqueous solution or slurry of Group IIA hydroxide of (i) to the final aqueous solution of mineral acid of (d);

(k) allowing the final aqueous solution or slurry of Group IIA hydroxide and the final aqueous solution of mineral acid of (j) to react;

(l) removing solid formed from (k) to give a final AGIIS solution or suspension; and (m) adding a predetermined amount of an additive to the final a solution or suspension of an AGIIS solution or suspension.

2. The method of claim 1 further comprising adding a Group IIA salt of a dibasic acid to the final aqueous mineral acid solution of (d).

3. The method of claim 2, wherein the mineral acid is sulfuric acid, the Group IIA hydroxide is calcium hydroxide, and the Group IIA salt of a dibasic acid is calcium sulfate.

* * * * *